United States Patent [19]

Dobson

[11] 4,440,602

[45] Apr. 3, 1984

[54] APPARATUS AND METHOD FOR MEASURING THE CONCENTRATION OF IONS

[75] Inventor: John V. Dobson, Hartlepool, England

[73] Assignee: National Research Development Corporation, London, England

[21] Appl. No.: 374,895

[22] Filed: May 4, 1982

[30] Foreign Application Priority Data

May 6, 1981 [GB] United Kingdom ............... 8113820

[51] Int. Cl.³ ............................................. G01N 27/46
[52] U.S. Cl. .................................... 204/1 T; 204/416; 204/419; 204/420
[58] Field of Search .......... 204/195 G, 195 M, 195 L, 204/1 A, 1 T, 195 R

[56] References Cited

U.S. PATENT DOCUMENTS

| | | | |
|---|---|---|---|
| 3,349,012 | 10/1967 | Solomons | 204/195 R |
| 3,411,993 | 11/1968 | Sambucetti et al. | 204/1 T |
| 3,523,872 | 8/1970 | Hersch et al. | 204/1 T |
| 4,118,194 | 10/1978 | Raleigh et al. | 204/195 R |
| 4,134,818 | 1/1979 | Pebler et al. | 204/1 T |
| 4,152,235 | 5/1979 | Dobson | 204/1 T |
| 4,357,143 | 10/1982 | Scott | 204/1 T |

Primary Examiner—R. L. Andrews
Assistant Examiner—Terryence Chapman
Attorney, Agent, or Firm—Cushman, Darby & Cushman

[57] ABSTRACT

Difficulties occur in finding an electrode which responds reliably to the concentration of some ions.

The concentration of a required ion in an electrolyte is measured by measuring the potential between first and second electrodes when the electrolyte is passed from the first electrode to the second electrode through a material which changes the concentration of another ion by an amount which depends on the concentration of the required ion. The first and second electrodes are reliable electrodes for measuring the concentration of the other ion.

7 Claims, 1 Drawing Figure

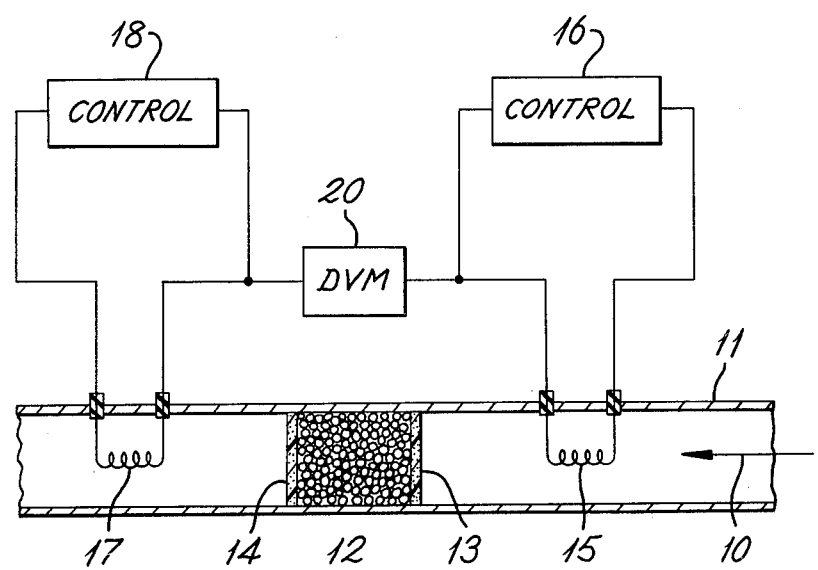

APPARATUS AND METHOD FOR MEASURING THE CONCENTRATION OF IONS

The present invention relates to ion selective electrodes and methods of measuring the ion concentration of certain ions, particularly Ca, Mg, Sr, Ba, Y and La. The ion selective electrodes are particularly, but not exclusively, pH sensitive, for example those employing palladium hydride or like hydrides.

A problem often arises in finding a reliable electrode which responds to the concentration of a particular ion, for example those mentioned above, and it is an object of the present invention to overcome this problem in certain areas.

According to the first aspect of the present invention there is provided apparatus for measuring the concentration of a predetermined ion in an electrolyte, comprising a duct through which flows, in operation, an electrolyte containing first ions, the concentration of which is to be measured, and second ions; two ion selective electrodes sensitive to the concentration of the second ions but not to that of the first ions, the ion selective electrodes being spaced apart along the duct, and material positioned between the ion sensitive electrodes which changes the concentration of the second ion in accordance with the concentration of the first ion.

Preferably the two ion selective electrodes are identical at least in their response to the second ions.

In order to use the apparatus, means are provided for deterimining the potential difference (P.D.) between the two ion sensitive electrodes, this P.D. being an indirect measure of the concentration of the first ions, provided either the flow rate of electrolyte along the duct is constant, when a quasi ionic equilibrium is set up, or the flow rate, though variable, is sufficiently slow for ionic equilibrium to be set up at the two electrodes.

According to a second aspect of the present invention there is provided a method of measuring the concentration of a predetermined ion in an electrolyte, comprising the steps of passing an electrolyte along a duct, the electrolyte containing first ions, the concentration of which is to be measured, and second ions; measuring an electromotive force which depends on the concentration of the second ions (but not the first ions) at a first location in the duct; passing the electrolyte through material positioned in the duct downstream of the first location, the material, when equilibrated with the electrolyte, changing the concentration of the second ion in accordance with the concentration of the first ion; and measuring, at a second location downstream from the said material, an electromotive force which depends on the concentration of the second ion (but not the first ion); the flow rate of the electrolyte along the duct being constant when a quasi electronic equilibrium is set up or sufficiently slow to allow ionic equilibrium to be set up in the regions of the first and second locations.

The problem of not being able to find a suitable electrode for measuring the concentration of a particular ion is solved by the present invention provided a material is available which changes the concentration of a further ion in accordance with the concentration of the said particular ion and also an ion sensitive electrode is known which is sensitive to the concentration of the further ion.

For example if the first ions are Ca, Sr, Ba, Y or La, Mg, the second ions may be hydrogen ions and the said material may be an almost insoluble mixture of a fatty acid, having, say, not less than eighteen carbon atoms in the homologous series, and the salt of that acid with the ion the concentration of which is to be measured. A suitable mixture for some applications is a mixture of stearic acid and the stearate formed with the ion of interest. Other suitable acids include nonylic, capric, undecylic, lauric, tridecylic, myristic and palmitic.

Preferably, where the second ions are hydrogen ions, the two ion sensitive electrodes are palladium hydride electrodes but other electrodes such as a glass electrode may be used. Other metals or alloys which form hydrides may be used instead of palladium. For example yttrium, zirconium, titanium, vanadium, or alloys of palladium with one or more of these metals, or alloys of two of these metals. In operation the metal or alloys are either precharged with hydrogen or charged with hydrogen in situ, for example in one of the ways described in British Specification No. 1,481,509. Hydride electrodes have many advantages over glass electrodes, in particular the continuously regenerated palladium hydride electrode is very robust in comparison to the glass electrode. It has a much lower electrical impedance and is much less susceptible to the effects of solid particulates and poisons on the electrode surface.

An embodiment of the invention will now be described, by way of example, with reference to the accompanying drawing which shows an ion sensitive electrode according to the invention.

An electrolyte containing one of the ions specifically mentioned above, for example Ca, the concentration of which is to be measured, is passed in the direction of the arrow 10 along a duct 11. The duct contains a mixture 12 of stearic acid and the stearate of the ion to be measured, for example calcium stearate. The mixture comprises particles as shown in the drawing. The mixture is contained by two inert porous discs 13 and 14, for example pourous P.T.F.E. discs.

Before encountering the mixture, the electrolyte passes a palladium hydride electrode 15 of one of the types described in the above mentioned British Specification. For example this electrode may comprise a coil of palladium wire containing hydrogen wound on a former (not shown), the wire being connected to a control circuit 16 which periodically samples the resistance of the wire. When the resistance of the wire is within predetermined limits, it is an indication that the hydrogen content of the hydride is low and the wire is automatically recharged with hydrogen, for example by electrolysis of the electrolyte in the duct 11, or by electrolysis of an electrolyte contained within a former for the wire, or by passing hydrogen along the palladium wire. When charging is by electrolysis of the electrolyte in the duct subsidiary electrodes (not shown) for this purpose are also located in the electrolyte.

After passing through the mixture 12, the electrolyte encounters another palladium hydride electrode 17 which is of the same type as the electrode 15, the hydrogen concentration in the electrode 17 being controlled by a circuit 18. Differences in electromotive forces (e.m.f.) between the electrodes 15 and 17 are measured in a digital voltmeter 20 but preferably a circuit, not shown, is provided to ensure that the e.m.f. measurements are not made when the electrodes 15 and 17 are being charged with hydrogen by electrolysis using the subsidiary electrodes.

The hydrogen ion concentration of the electrolyte is compared before and after passage through the mixture 12 by measuring the P.D. between the electrodes 15 and 17, this P.D. being proportional to the difference in concentration between hydrogen ions or pH and the electrodes 15 and 17. When the electrolyte reaches the mixture 12 it is equilibrated with the mixture and as a result the concentration of hydrogen ions is changed in proportion to the concentration of the ion the concentration of which is to be measured. As far as ionic processes are concerned operation is similar to that described in a paper by Al Attar and W. H. Beck entitled "Alkaline Earth and Lanthanum Ion Electrodes of the Third Kind Based on the Hydrogen Ion Responsive Glass Electrode. Thermodynamic Solubility Products of Long Chain Normal Fatty Acids and Their Alkaline Earth and Lanthanum Salts in Water", Journal of Electroanalytical Chemistry, Volume 27 (1970) pages 59–67.

An equilibrium is set up between the ions of interest and the ions formed when the stearic acid and the stearate ionise. The resulting concentration of the hydrogen ions depends on the concentration of the ion of interest. Thus the concentration of hydrogen ions at the electrode 17 is compared with the concentration at the electrode 15 by measuring the P.D. between these electrodes, and the P.D. measured is proportional to the concentration of the ion of interest.

For example the following two equations express the equilibria when stearic acid ionises and calcium ions are present:

$$C_{17}H_{35}COOH\ (S) \rightleftharpoons C_{17}H_{35}COO^-(aq) + H^+(aq) \quad \text{equilibrium 1,}$$

and $$2C_{17}H_{35}COO^-(aq) + Ca^{2+}(aq) \rightleftharpoons Ca(C_{17}H_{35}COO)_2(S) \quad \text{equilibrium 2}$$

The presence of free $Ca^{2+}$ ions in solution and the existence of equilibrium 2 upsets equilibrium 1. Thus because of the stearate ion, the hydrogen ion concentration alters in direct proportion.

It will be evident that the invention may be put into practice in many other ways in addition to the way specifically described above. For example different ion selective electrodes may be used and the material which changes the concentration of one ion in proportion to the concentration of another ion may be of many different types. The ion sensitive electrode is selected according to the type of ion to be detected and the said material used. The configuration of the material and the two electrodes may, of course, be different from that shown in the drawing.

I claim:

1. A method of measuring the concentration of a predetermined ion in an electrolyte, comprising the steps of passing an electrolyte along a duct, the electrolyte containing first ions, the concentration of which is to be measured, and second ions, measuring an electromotive force which depends on the concentration of the second ions (but not the first ions) at a first location in the duct, passing the electrolyte through material positioned in the duct downstream of the first location, the material, when equilibrated with the electrolyte, changing the concentration of the second ion in accordance with the concentration of the first ion, and measuring, at a second location downstream from the said material, an electromotive force which depends on the concentration of the second ion (but not the first ion), the flow rate of the electrolyte along the duct being constant when a quasi electronic equilibrium is set up or sufficiently slow to allow ionic equilibrium to be set up in the regions of the first and second locations.

2. A method according to claim 1 for measuring the concentration of the ions of one of the following:

Ca, Mg, Sr, Ba, Y and La, wherein the said material is an almost insoluble mixture of a fatty acid and the salt of that acid with the ion whose concentration is to be measured.

3. Apparatus for measuring the concentration of a predetermined ion in an electrolyte, comprising a duct through which flows, in operation, an electrolyte containing first ions, the concentration of which is to be measured, and second ions, two ions selective electrodes sensitive to the concentration of the second ions but not to that of the first ions, the ion selective electrodes being spaced apart along the duct, and material positioned between the ion sensitive electrodes which changes the concentration of the second ion in accordance with the concentration of the first ion.

4. Apparatus according to claim 3 for measuring the concentration of the ions of one of the following:

Ca, Mg, Sr, Ba, Y and La, wherein the said material is an almost insoluble mixture of a fatty acid and the salt of that acid with the ion whose concentration is to be measured.

5. Apparatus according to claim 3 wherein the two ion selective electrodes comprise metals or alloys which can be charged with hydrogen to form hydrides.

6. Apparatus according to claim 4 wherein each molecule of the fatty acid has not less than eighteen carbon atoms.

7. Apparatus according to claim 5 wherein the two ion selective electrodes comprise palladium and means are provided for charging the electrodes with hydrogen while the electrodes are in situ.

* * * * *